(12) United States Patent
Ferguson et al.

(10) Patent No.: US 11,523,813 B1
(45) Date of Patent: Dec. 13, 2022

(54) SOFT BUTTON ASSEMBLY AND PROCEDURE

(71) Applicant: RIVERPOINT MEDICAL, LLC, Portland, OR (US)

(72) Inventors: Patrick Edward Ferguson, Portland, OR (US); Patrick Joseph Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 823 days.

(21) Appl. No.: 16/364,514

(22) Filed: Mar. 26, 2019

(51) Int. Cl.
*A61B 17/04* (2006.01)

(52) U.S. Cl.
CPC .... *A61B 17/0401* (2013.01); *A61B 2017/042* (2013.01); *A61B 2017/0404* (2013.01); *A61B 2017/0459* (2013.01)

(58) Field of Classification Search
CPC ........ A61B 17/0401; A61B 2017/0404; A61B 2017/042; A61B 2017/0459
See application file for complete search history.

(56) References Cited

U.S. PATENT DOCUMENTS

| | | | |
|---|---|---|---|
| 5,306,301 A | 4/1994 | Graf et al. | |
| 6,231,654 B1 | 5/2001 | Elwakil | |
| 6,517,578 B2 | 2/2003 | Hein | |
| 6,533,802 B2 | 3/2003 | Bojarski et al. | |
| 7,959,650 B2 | 6/2011 | Kaiser | |
| 8,088,130 B2 | 1/2012 | Kaiser et al. | |
| 8,118,836 B2 | 2/2012 | Denham et al. | |
| 8,460,379 B2 | 6/2013 | Albertorio et al. | |
| 9,179,950 B2 * | 11/2015 | Zajac | A61B 17/8061 |
| 9,204,960 B2 | 12/2015 | Albertorio et al. | |
| 9,216,078 B2 | 12/2015 | Conner et al. | |
| 9,333,069 B2 | 5/2016 | Denham | |
| 9,357,990 B2 | 6/2016 | Ferguson et al. | |
| 9,629,709 B2 | 4/2017 | Ferguson et al. | |
| 9,867,691 B2 | 1/2018 | Ferguson et al. | |
| 9,963,319 B2 | 5/2018 | Ferguson | |
| 10,070,856 B1 | 9/2018 | Black et al. | |
| 10,194,900 B2 | 2/2019 | Ferguson | |
| 2002/0052629 A1 | 5/2002 | Morgan et al. | |

(Continued)

OTHER PUBLICATIONS

Boyle, M.J. et al., ACL TightRope Scientific Update, Arthrex, Inc., LA1-00021-EN_B, pp. 1-2, 2016.

(Continued)

*Primary Examiner* — Ashley L Fishback
(74) *Attorney, Agent, or Firm* — Timothy E. Siegel Patent Law, PLLC; Timothy E. Siegel

(57) ABSTRACT

A suture construct having a soft button, defining a multiplicity of first apertures and a set of second apertures. Also, a suture loop assembly has a suture defining a lumen and forming a double loop, formed by a double trap having a first end and a second end, formed in a trap region of the suture, and in which a first portion of the suture is threaded through the trap region lumen from the first end to the second end and the first portion extends out from the second end, and a second portion of the suture is threaded through the trap region lumen from the second end to the first end, and the second portion extends out from the first end. Finally, the double loop passes through the set of second apertures of the soft button.

7 Claims, 8 Drawing Sheets

(56) References Cited

U.S. PATENT DOCUMENTS

| | | |
|---|---|---|
| 2005/0149118 A1 | 7/2005 | Koyfman |
| 2007/0185532 A1 | 8/2007 | Stone et al. |
| 2007/0233151 A1 | 10/2007 | Chudik |
| 2008/0177302 A1 | 7/2008 | Shurnas |
| 2008/0312689 A1 | 12/2008 | Denham et al. |
| 2009/0312776 A1 | 12/2009 | Kaiser et al. |
| 2009/0318961 A1 | 12/2009 | Stone et al. |
| 2010/0268273 A1 | 10/2010 | Albertorio et al. |
| 2011/0060366 A1* | 3/2011 | Heim ............... A61B 17/7064 606/247 |
| 2011/0087280 A1 | 4/2011 | Albertorio |
| 2011/0098727 A1 | 4/2011 | Kaiser et al. |
| 2011/0270278 A1 | 11/2011 | Overes et al. |
| 2012/0024134 A1 | 2/2012 | Dow et al. |
| 2012/0046693 A1 | 2/2012 | Denham |
| 2012/0046746 A1 | 2/2012 | Konicek |
| 2012/0123541 A1 | 5/2012 | Albertorio et al. |
| 2012/0197271 A1 | 8/2012 | Astorino et al. |
| 2012/0290002 A1 | 11/2012 | Astorino |
| 2013/0110165 A1 | 5/2013 | Burkhart et al. |
| 2013/0317544 A1 | 11/2013 | Ferguson et al. |
| 2015/0157449 A1 | 6/2015 | Gustafson |
| 2015/0173739 A1 | 6/2015 | Rodriguez et al. |
| 2016/0128684 A1 | 5/2016 | Stone et al. |
| 2017/0360437 A1 | 12/2017 | Ferguson et al. |
| 2018/0008257 A1 | 1/2018 | Ferguson et al. |
| 2018/0338756 A1 | 11/2018 | Black et al. |
| 2019/0076139 A1* | 3/2019 | Dreyfuss ............... A61F 2/0811 |

OTHER PUBLICATIONS

Watson, John, "Endobutton CL Ultra fixed-length cortical suspension device vs. adjustable-loop fixation designs: Review of mechanical data", Bone & Joint Science, vol. 4, No. 4, pp. 1-9, Oct. 2004.

Patent Cooperation Treaty (PCT), International Searching Authority, Application No. PCT/US17/26353, International Search Report and Written Opinion, dated Aug. 1, 2017.

Barrow, AE et al., Femoral Suspension Devices for Anterior cruciate ligament reconstruction: do adjustable loops lengthen?, Am J Sports Med. Feb. 2014; 42(2):343-9. doi: 10.1177/0363546513507769. Epub Oct. 24, 2013.

"Advanced ACL/PCL Graft Fixation Options . . . Simplified", TightRope Implant, Arthrex, Inc., LB1-0179-EN-B, pp. 1-12, 2016.

McCarty, Eric, M.D., "ACL Reconstruction" Biomet Sports Medicine, Mar. 2009.

* cited by examiner

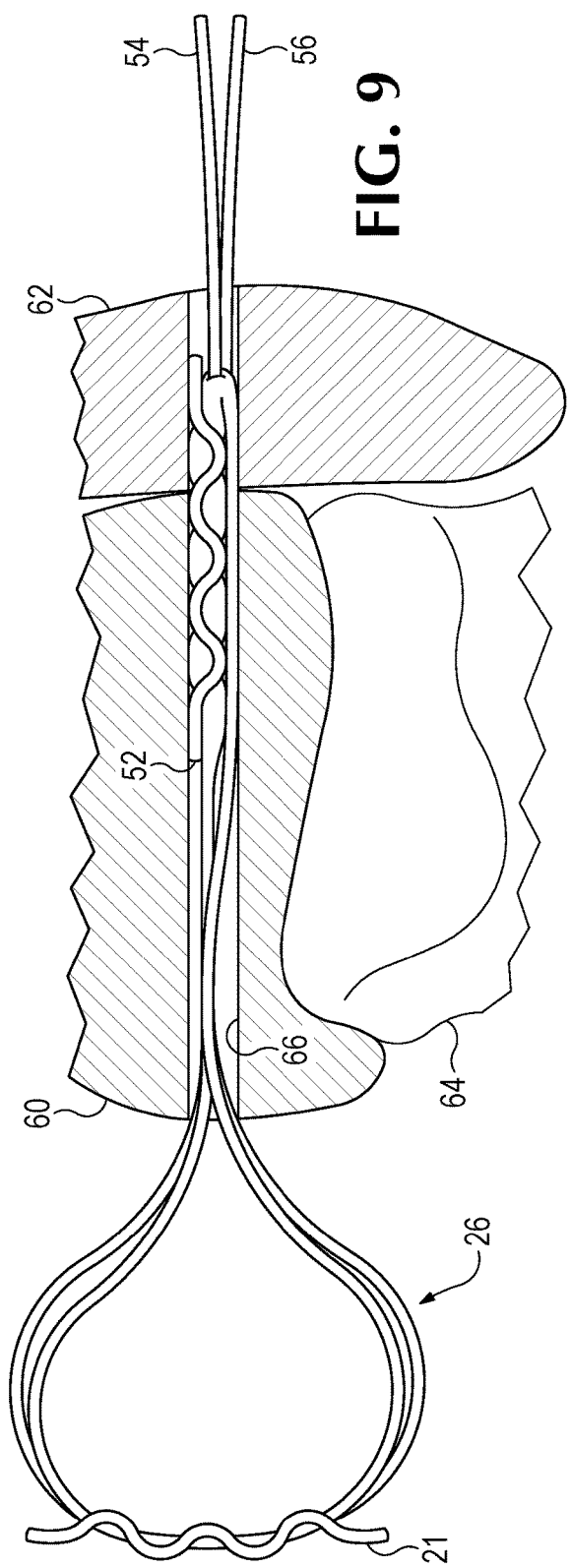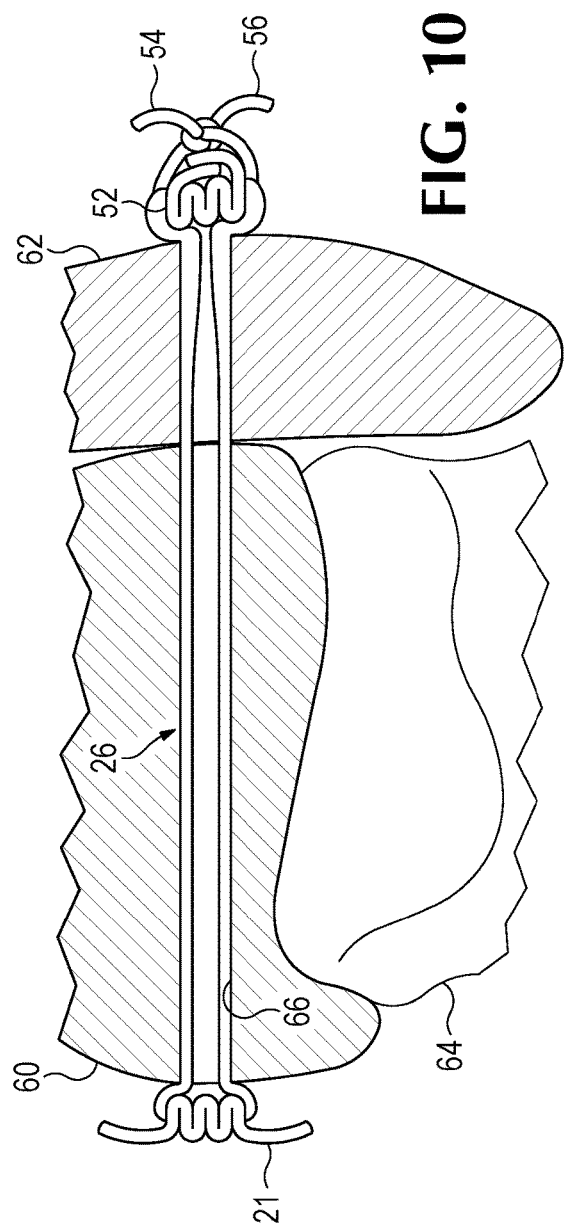

SOFT BUTTON ASSEMBLY AND PROCEDURE

BACKGROUND OF THE INVENTION

There are many different types of surgeries in which a button, typically formed of titanium, is passed through a passageway that has been drilled in a bone and is then reoriented to lie flat on the bone surface. The button is passed through the hole with suture already looped through a pair of holes in the button, and the suture is used to either tie bones together or supports a tendon graft. The button performs a number of functions. First, it can be reoriented so that its widest dimension is over the hole, thereby being able to anchor the suture over the passageway that it was passed through with the button's long dimension coincident with the passageway. Second, as the button is rigid, it spreads out the force that will be applied to the suture, over an area of the bone. If the same force where applied to a very small area, right at the rim of the passageway, it could break the bone surface, causing failure of the correction performed by the surgery.

Unfortunately, the button also sets a minimum diameter for the drilled passageway. The greater this diameter, the greater the disruption to the bone, and potential pain to the patient during recovery. Moreover, the rigidity of the button is not an unmitigated positive, and any nonconformity of the button surface facing the bone and the bone surface facing the button could cause an area of high pressure to be created, potentially breaking some of the bone.

SUMMARY OF INVENTION

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a method for affixing a suture loop to a bone structure that utilizes a suture construct that includes soft button defining a multiplicity of first apertures and a set of second apertures, and a suture loop assembly, made of a suture defining a lumen and forming a double loop, formed by a double trap having a first end and a second end, formed in a double trap portion of the suture, and in which a first portion of the suture is threaded through the trap region lumen from the first end to the second end and the first portion extends out from the second end, and a second portion of the suture is threaded through the trap region lumen from the second end to the first end, and the second portion extends out from the first end to a second end; and wherein the double loop is threaded through the set of second apertures in the soft button. The method includes drilling through the bone structure, thereby creating a passageway, having a first and a second rim, and pulling the soft button through the passageway, from the first rim through the second rim, together with the first portion and the second portion, with the remainder of the loop extending through the passageway. The loop is then anchored at a position opposed to the soft button and the first and second portions are pulled to bring the suture loop into tension, with the soft anchor resting against the second rim.

In a second separate aspect, the present invention may take the form of a suture construct having a soft button, defining a multiplicity of first apertures and a set of second apertures. Also, a suture loop assembly has a suture defining a lumen and forming a double loop, formed by a double trap having a first end and a second end, formed in a trap region of the suture, and in which a first portion of the suture is threaded through the trap region lumen from the first end to the second end and the first portion extends out from the second end, and a second portion of the suture is threaded through the trap region lumen from the second end to the first end, and the second portion extends out from the first end. Finally, the double loop passes through the set of second apertures of the soft button.

In a third separate aspect, the present invention may take the form of a method of making a suture construct, that utilizes a soft button, defining a multiplicity of first apertures and a set of second apertures and a length of suture material defining a lumen, the length have a first end and a second end. In the method, the first end of the length of suture material is passed through the set of second apertures, so that the length of suture material is engaged to the soft button. Then the suture material is breached at a first location and the first end is introduced into the lumen at the first location. Also, the suture material is breached at a second location, and the first end is pulled out of the lumen at the second location, thereby creating a first loop of suture material. Then, the second end of the suture material is passed through the set of second apertures, so that two portions of the length of suture material are engaged to the soft button. Finally, the second end of the suture material is passed into the lumen at the second location and is pulled out of the lumen at the first location, thereby creating an additional loop of suture material, which together with the first loop forms a double loop.

BRIEF DESCRIPTION OF DRAWINGS

Various embodiments of the invention are disclosed in the following detailed description and accompanying drawings.

FIG. 9 shows the same view as FIG. 8, but at a further stage of the syndesmosis correction surgery, as a portion of a corrective apparatus is being pulled through the drilled hole.

FIG. 10 shows the same view as FIG. 8, at a final stage of the syndesmosis correction surgery, showing the corrective apparatus placed into service.

DETAILED DESCRIPTION AND EMBODIMENTS

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

To assist the description of the scope and its components the coordinate terms ["proximal" and "distal"] are used to describe the disclosed embodiments. The terms are used consistently with the description of the exemplary applications and are in reference to [the head of a user]. In other words, [proximal components are nearer to the user than distal components].

Figure 1:
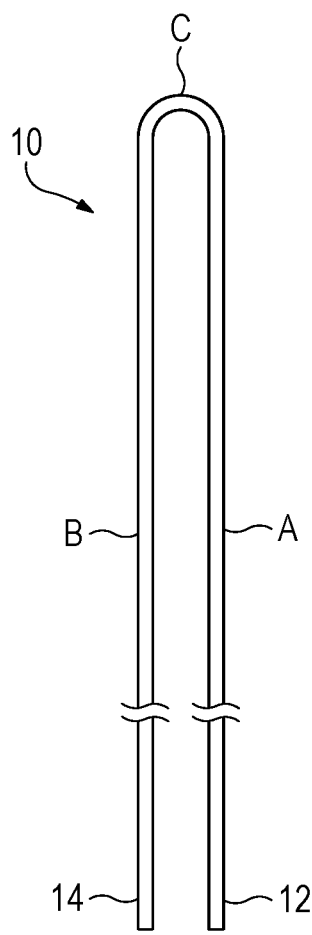
FIG. 1 shows a length of suture material, with portions and segments labelled.
Figure 2:
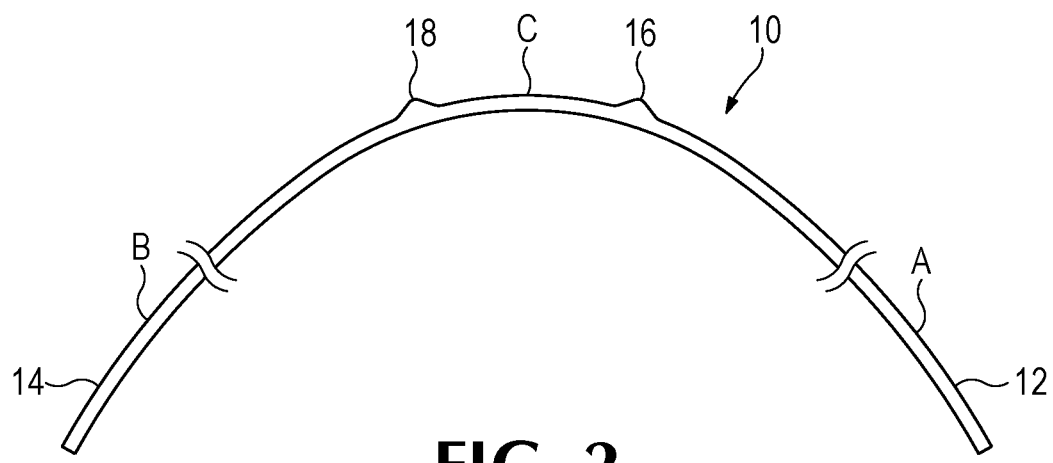
FIG. 2 shows the length of suture material of FIG. 1, having two locations prepared for piercing.

FIG. 1 shows a length of fiber or suture 10, bent in a U-shape and having a first tail 12 and an opposed second tail 14. Also, three thirds of the suture 10 are indicated, a first third A, an opposing third B, and a central third C. In a preferred embodiment, suture 10 is a braid that defines an inner lumen. As shown in FIG. 2, the suture 10 is preferably fluffed at the entry point 16 and exit point 18 to make it easier for a lacing tool 22 (FIG. 3) to be inserted through a double trap section 20. One end of the lacing tool 22 can include a handle to allow a user to position, guide, push, and pull the tool. The lacing tool 22 also includes a main body that is preferably substantially linear and having a diameter, or cross-section, small enough to thread through the suture 10. The end of the lacing tool 22 opposite of the handle can include a hinged barb 24 to allow for coupling to the suture 10. The hinge allows the barb 24 to have a lower profile when traversing through the inside of suture 10 while minimizing the chance of snags. Other means for coupling to the suture 10 are readily contemplated and can nonexclusively include one or more barbs (hinged or unhinged) hooks, clamps (such that can be opened and closed by the handle) and the like, for example. Said means for coupling preferably should not prevent or hinder the lacing tool 22 from being pushed into or pulled out of the inside of the suture 10. In a preferred embodiment fiber or suture 10 is made of ultra-high molecular weight polyethylene (UHMWPE).

Figure 3:
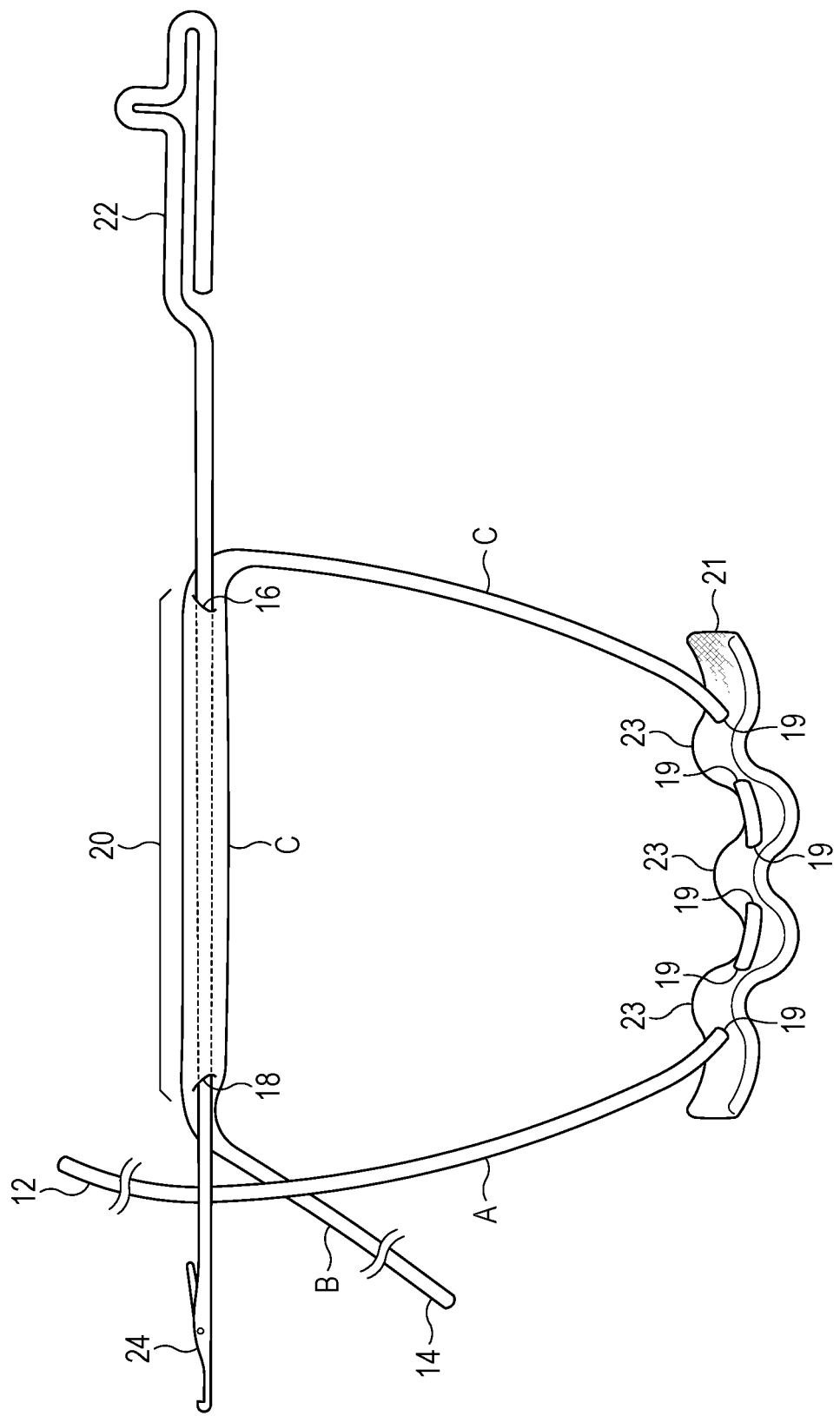
FIG. 3 shows the length of suture material of FIG. 1, with a soft button added and a loop in the process of being formed, using a lacing tool.

As depicted in FIG. 3, suture 10 has been threaded through six apertures 19 of a soft button 21. Soft button 21 forms a set of three folds 23, as a result. In a preferred embodiment, soft button 21 is a piece of woven material, naturally having apertures in the interstices of the weave. In an alternative preferred embodiment, soft button 21 is a sheet of nonwoven material in which apertures have been created, for example a sheet of expanded Poly Tetra Fluoroethylene (ePTFE), which is created by a rapid pull on a sheet of PTFE, which creates numerous small apertures. In another preferred embodiment a sheet of flexible polymeric material is laser drilled to create the apertures. As will be discussed further below, in all of these embodiments, further apertures, in addition to apertures 19, are created, for tissue ingrowth after implantation.

A trap section 20 is defined, between points 16 and 18, and the barb 24 of the lacing tool 22 is pushed into the lumen of the suture 10 at the fluffed entry point 16. The barb 24 is pushed through the inside of the trap section 20 and guided outward through the fluffed exit point 18. Suture end 12 is then grasped by the barb 24 and drawn through exit point 18 and out through point 16. The result of this operation (not shown) is that tail 12 extends through trap section 20, exiting at point 16, and forming a loop 26 (FIG. 4).

Figure 4:
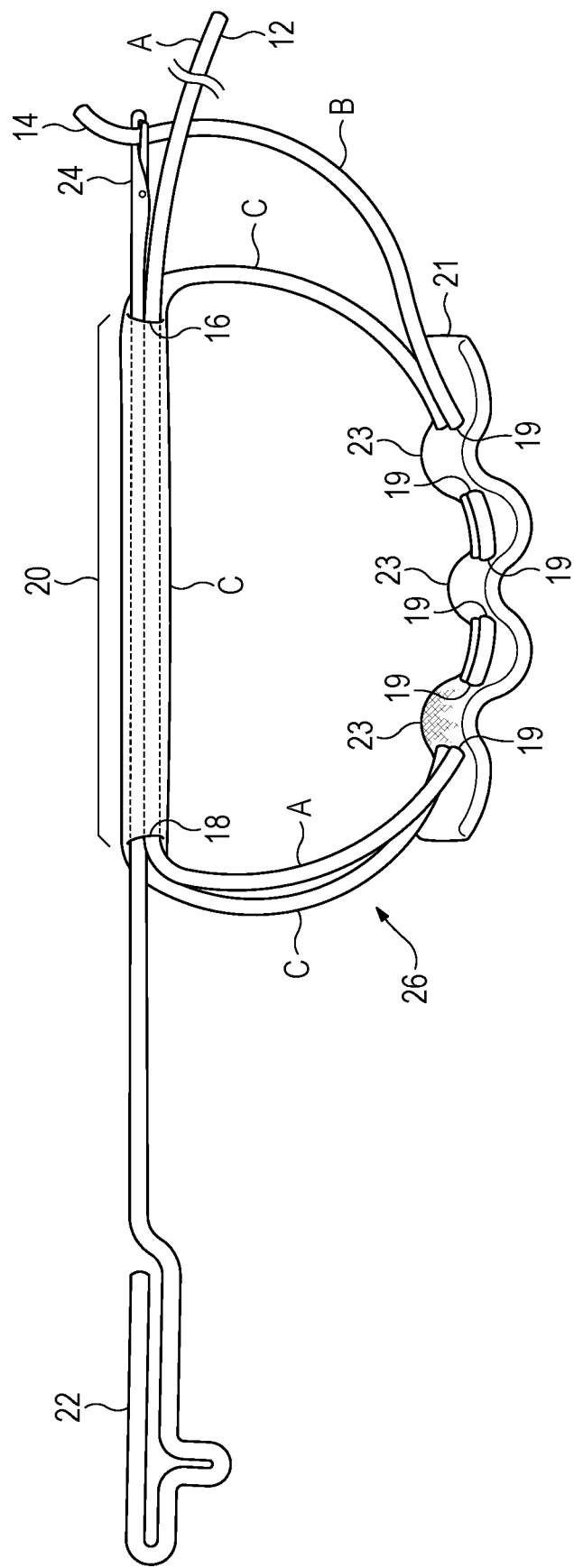
FIG. 4 shows the length of suture material of FIG. 1, engaged to the soft button of FIG. 3, and with a second loop in the process of being formed.
Figure 5:
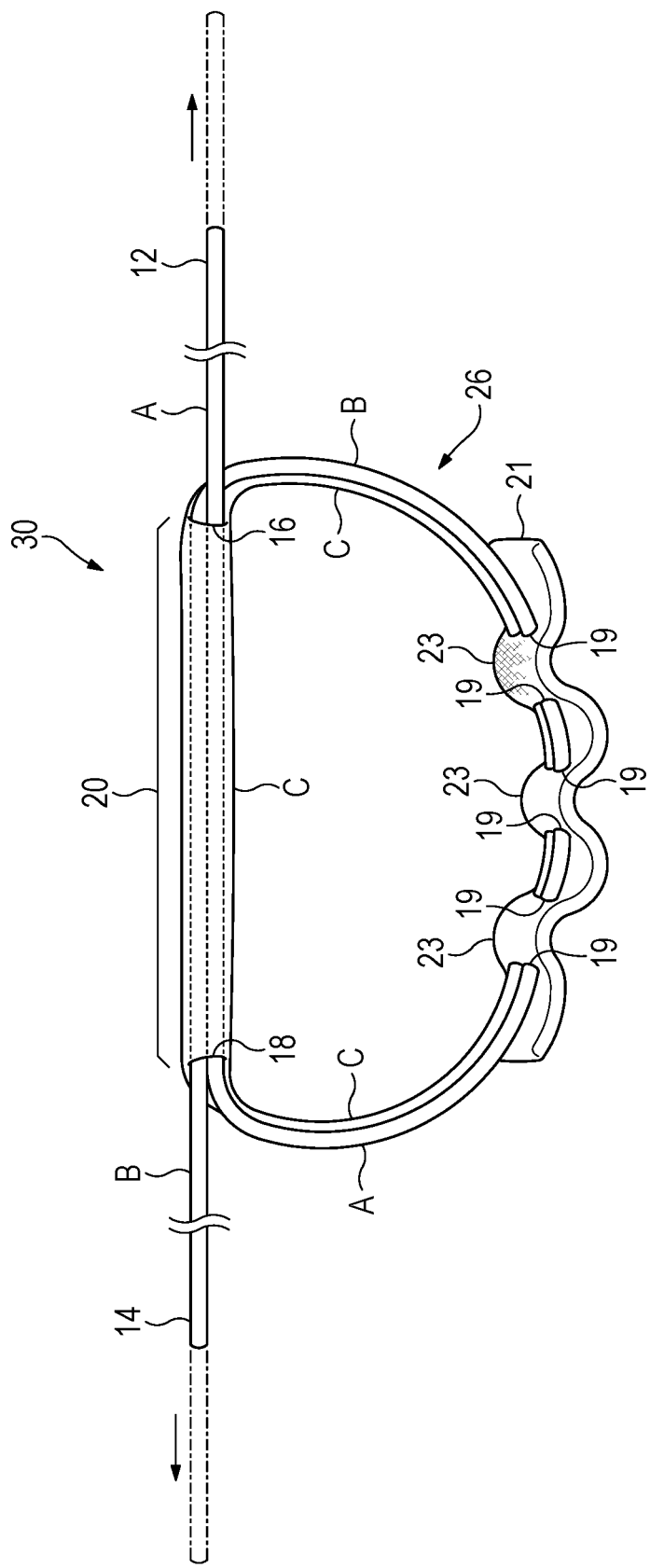
FIG. 5 shows a completed assembly, with a double loop formed and a soft button.

Referring to FIG. 4, second tail 14 is threaded through apertures 19, seized by barb 24 and drawn back through trap section 20, entering through second point 18 and exiting through first point 16. The finished suture construct 30 is shown in FIG. 5, having a double loop 26, and a tail (12 and 14) extending out of loop 26 in either direction. Trap section 20 is now a double trap 20, having portion A of suture 10 going through double trap 20 from second point 18 to first point 16 and portion B of suture 10 going through double trap 20 in the opposite direction.

Figure 6A:
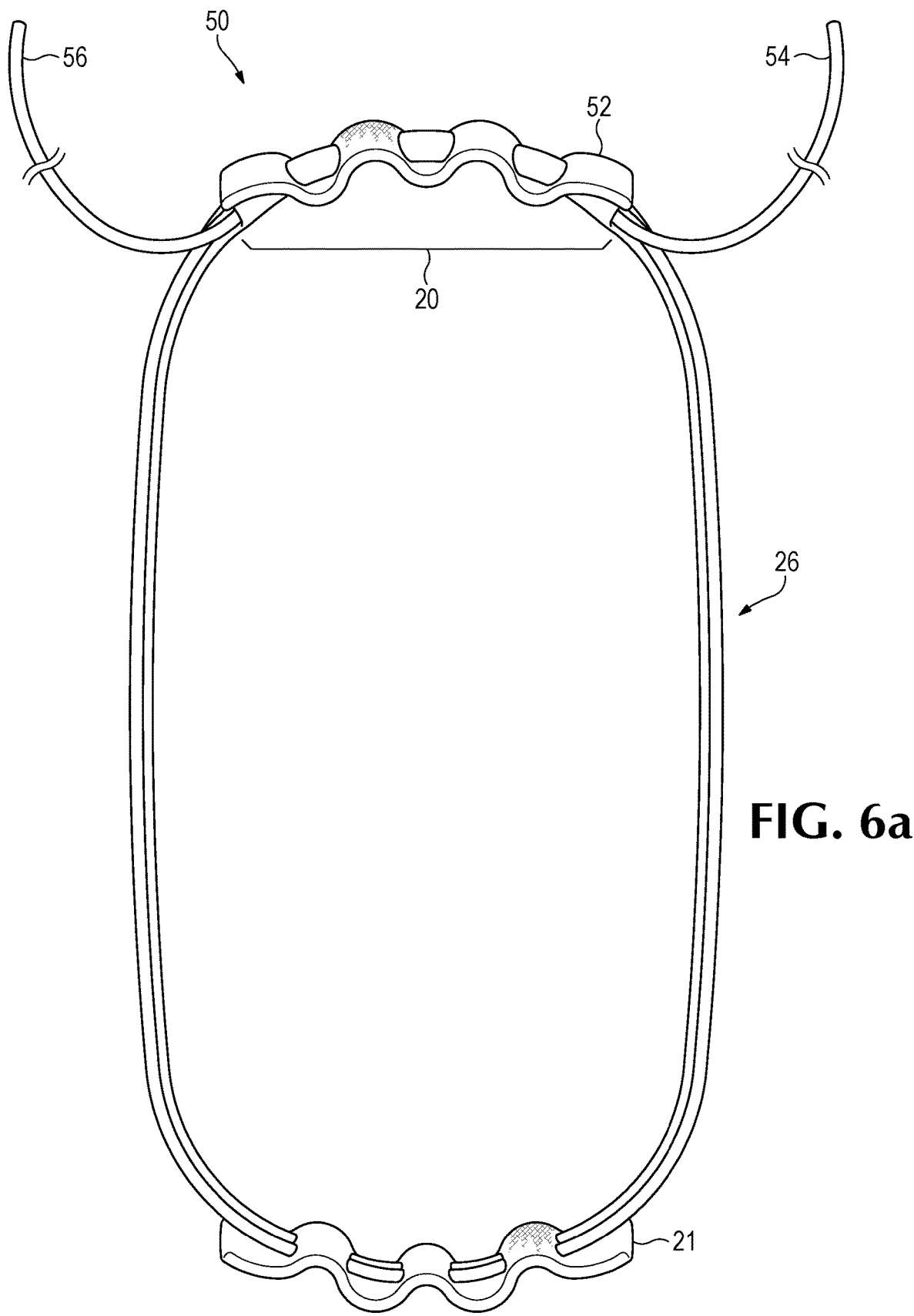
FIG. 6*a* shows an alternative embodiment of a completed assembly, having a soft button on either end.
Figure 6B:
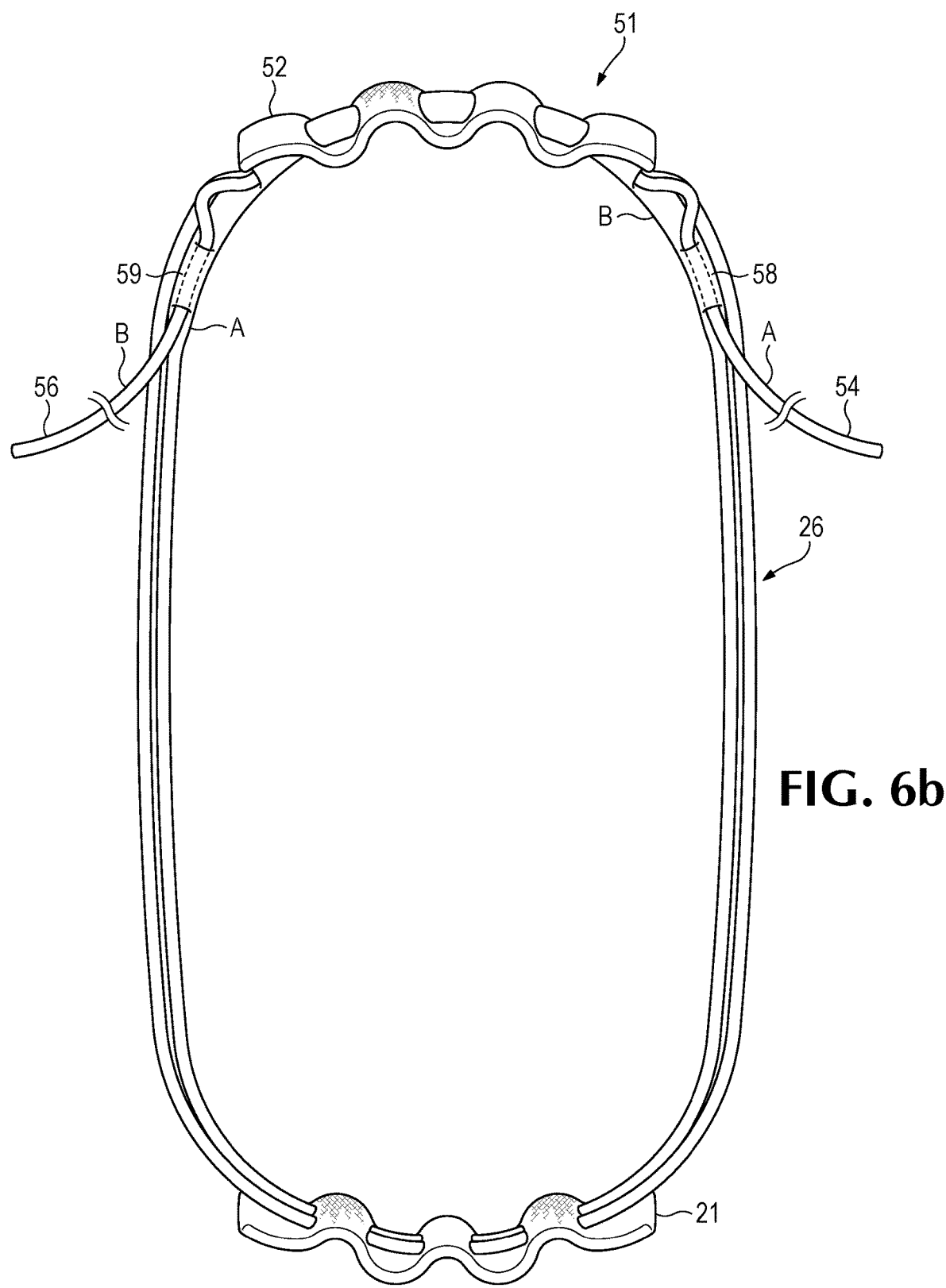
FIG. 6*b* shows an additional alternative embodiment of a completed assembly, having an additional trap on either side of the double trap section.

FIG. 6a shows an alternative embodiment 50 of the construct 30 shown in FIG. 5, wherein a second soft button 52 having been placed over trap section 20, at the beginning of the process of making, now forms an integral part of the construct 50. Suture ends 54 and 56 extend out from the reminder of construct 50. FIG. 6b shows an additional alternative embodiment 51, similar to construct 50, but having two additional traps 58 and 59, using the designations introduced in FIGS. 1-5, in trap 58, section A passes through the lumen of section B, and in trap 59, section B passes through the lumen of section A. Constructs 50 and 51 both permit the size of loops 26 to be adjusted, with construct 51 being more resistant to re-enlargement due to force application during use.

Figure 7:
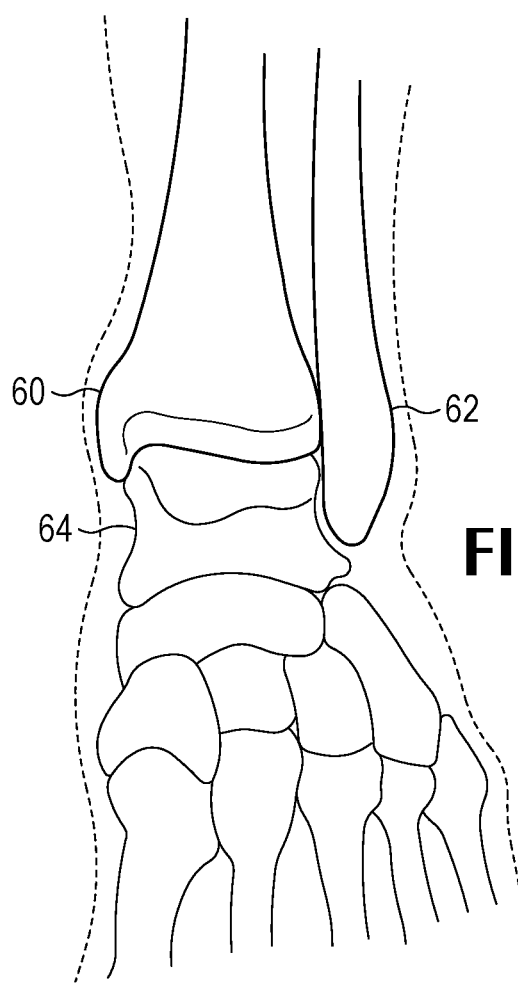
FIG. 7 shows a front view of the bone structure of the bottom portion of a human leg.
Figure 8:
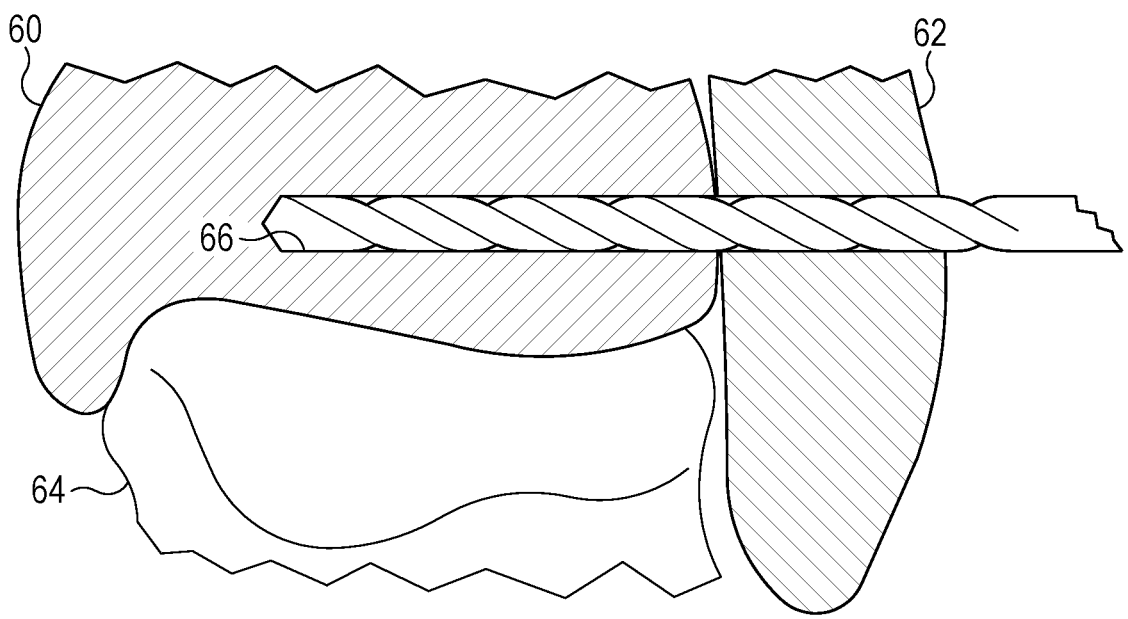
FIG. 8 is a detail view of the bottom portion of the structure shown in FIG. 7, as a hole is being drilled through the bones of the calf, as the beginning part of a syndesmosis correction surgery.

FIG. 7 is an illustration of the bone structure of the lower part of a human calf. The tibia 60 and fibula 62 are supported by the talus 64, and in turn support the femur (not shown). The tendons that couple the tibia 60 and fibula 62 can be strained and stretched to the point of not performing properly, thereby impeding the function of a person, and causing that person (henceforth "patient") pain. In some cases, the fibula 62 is broken or fractured. Currently, to fix this condition, typically a construct having two hard buttons is used. Referring to FIG. 8, a hole is drilled through tibia 60 and fibula 62, and a hard button, having four apertures and with suture material looped through two of the apertures is passed through the drilled hole, and reoriented to lay flat on the exterior side of the tibia 60, with the suture material extending through the drilled hole to the fibula side. A second button is used to brace the construct on the fibula side, against the fibula 62, which, if fractured, is protected and repaired by a plate (not shown). The suture loop extending between the two buttons, braces the tibia and fibula together, relieving the complex tendon system connecting the two bones, of a great deal of stress and permitting the tendon system to heal. Although a syndesmosis correction surgery of this sort can relieve a patient of a great deal of pain and restore functioning, it is not without its drawbacks. For many patients, subcutaneous fat is at a minimum in the regions in which the hard buttons are placed, and this is also an area that may come into contact with constricting footwear, potentially causing discomfort. Additionally, the button size places a minimum on the width of the required drilled hole. The larger the drilled hole the more disruption there is to the living tissue of the tibia 60 and fibula 62. The drilled hole potentially weakens the bones, particularly the fibula 62, which due to its small size may be more vulnerable to disruption.

As shown in FIG. 9, construct 50 may be pulled through drilled hole 66 using one or both of ends 54 and 56, using known surgical techniques. Soft button 52 is then reoriented and ends 54 and 56 tied together as shown in FIG. 10, to retain soft button 52 at the end of the drilled hole. Soft button 21 provides support against being pulled into drilled hole 66, on the tibia side. It is typical for a patent to be advised to avoid any stress on an implant, such as construct 50, for a period of a few weeks after surgery. This process may be helped by an immobilizing device such as a boot. During this period soft buttons 21 and 52 will experience granulation tissue ingrowth and be gradually transformed into a hardened mass of granulation tissue and the material of the soft buttons 21 and 52. By the time the patient recovers, a hardened granuloma will have formed about the soft buttons 21 and 52, thereby resisting forces that otherwise might pull the soft buttons 21 and 52 back into the drilled hole 66. The pressure of the skin against the buttons 21 and 52 tend to flatten these buttons, creating greater patient comfort. The granulomas that form do not have the sharp corners of man-made hard buttons used previously. In addition, the deformability of buttons 21 and 52 allows passage through a smaller drilled hole than would be necessary for a standard hard button.

Although the soft button 21 has been described with respect to syndesmosis correction surgery, the same basic technique may be used in other surgeries where a button is used, for example anterior cruciform ligament (ACL) graft implant surgery, where button 21 of construct 30 would be placed on the cancellous bone of the femur, with a graft suspended from the loop 26. Again, tissue in growth renders button 21 into a hard mass of granulation tissue and button material. Still, it will be a more advantageous shape and composition to avoid creating discomfort to the patient. The soft button 21 may be passed through a drilled passageway that is narrower than would be the case if a hard button were used.

The disclosed embodiments are illustrative, not restrictive. While specific configurations of the suture constructs and surgical methods have been described, it is understood that the present invention can be applied to a wide variety of surgical constructs and surgical methods. There are many alternative ways of implementing the invention.

What is claimed is:

1. A method for affixing a suture loop to a bone structure, comprising:
   a) providing a suture construct, including:
      i. a soft button, comprising a sheet of flexible material defining a multiplicity of first apertures and a set of second apertures; and
      ii. a suture loop assembly, a suture defining a lumen and forming a double loop, formed by a double trap having a first end and a second end, formed in a double trap region of said suture, and in which a first portion of said suture is threaded through said double trap region of said lumen from said first end to said second end and said first portion extends out from said second end, and a second portion of said suture is threaded through said trap region lumen from said second end to said first end, and said second portion extends out from said first end to a second end; and
      iii. wherein said double loop is threaded through said set of second apertures in said soft button;
   b) drilling through said bone structure, thereby creating a passageway, having a first and a second rim;
   c) pulling said soft button through said passageway, from said first rim through said second rim, together with said first portion and said second portion, with the remainder of said loop extending through said passageway;
   d) anchoring said loop at a position opposed to said soft button; and
   e) pulling on said first and second portions to bring said suture loop into tension, with said soft button resting against said second rim.

2. The method of claim 1, wherein said first and second apertures are interstices of a weave of biocompatible fibers, comprising said sheet of flexible material.

3. The method of claim 1, wherein said first and second apertures are laser-drilled apertures in a sheet of polymeric material, comprising said sheet of flexible material.

4. The method of claim 1, wherein said soft button is a first soft button and said suture loop assembly further comprises a second soft button, opposed to said first soft button and further wherein said step of anchoring said suture loop at a position opposed to said first soft button is performed by said second soft button being positioned so that it braces against said first rim.

5. The method of claim 4, wherein said bone structure is a lower calf structure of said patient, including a tibia and fibula, and wherein said drilling is performed through said tibia and fibula, and wherein said loop holds said tibia and fibula together, after implantation, with said first.

6. The method of claim 1, further comprising leaving said soft button in said patient and thereby permitting tissue ingrowth into said first apertures and creating a part tissue part button-material button that resists being pulled back through said passageway.

7. The method of claim 1, wherein set of second apertures consists of at least six apertures, and wherein said soft button is formed into at least three folds by said double loop passing through said six apertures.

\* \* \* \* \*